(12) United States Patent
Staroselsky et al.

(10) Patent No.: US 7,549,339 B2
(45) Date of Patent: Jun. 23, 2009

(54) INVERSE THERMAL ACOUSTIC IMAGING PART INSPECTION

(75) Inventors: Alexander Staroselsky, Avon, CT (US); Thomas J. Martin, East Hampton, CT (US); Carroll V. Sidwell, Wethersfield, CT (US); Zhong Ouyang, Glastonbury, CT (US); Kevin D. Smith, Glastonbury, CT (US)

(73) Assignee: United Technologies Corporation, Hartford, CT (US)

( * ) Notice: Subject to any disclaimer, the term of this patent is extended or adjusted under 35 U.S.C. 154(b) by 421 days.

(21) Appl. No.: 11/515,610

(22) Filed: Sep. 5, 2006

(65) Prior Publication Data

US 2008/0053234 A1   Mar. 6, 2008

(51) Int. Cl.
G01N 29/04 (2006.01)
G01N 25/72 (2006.01)

(52) U.S. Cl. .................. 73/601; 250/341.6; 250/341.1; 702/40; 702/109; 73/606

(58) Field of Classification Search ........................ None
See application file for complete search history.

(56) References Cited

U.S. PATENT DOCUMENTS

| 5,711,603 | A | 1/1998 | Ringermacher et al. | |
| 6,236,049 | B1 * | 5/2001 | Thomas et al. | 250/341.6 |
| 6,399,948 | B1 | 6/2002 | Thomas et al. | |
| 6,730,912 | B2 | 5/2004 | Sun et al. | |

(Continued)

FOREIGN PATENT DOCUMENTS

| DE | 10059854 A1 * | 6/2002 |
| EP | 1 431 755 | 6/2004 |
| EP | 1517138 A1 * | 3/2005 |

OTHER PUBLICATIONS

Australian Search Report for Singapore Application No. 200706413-2, Mar. 26, 2008.

(Continued)

*Primary Examiner*—Hezron Williams
*Assistant Examiner*—Rose M Miller
(74) *Attorney, Agent, or Firm*—Carlson, Gaskey & Olds, P.C.

(57) ABSTRACT

A method of identifying a flaw in a part is provided that includes vibrating a part to induce heat. The heat originates in any flaws in the part. A thermal image is obtained using, for example, an infrared camera. A mathematical representation of the thermophysics, such as the heat conduction or thermal energy equations using the boundary element method or finite element method is used to identify a source and an intensity of the heat identified with the thermal image. Using the source and intensity of the heat, flaw characteristics for the part can be determined. The method is employed using an inspection system that includes a vibration device for vibrating the part. An imaging device, such as an infrared camera, measures temperature on the surface of the part. An assumption is made or additional measurements are taken to obtain values for surface flux or surface heat transfer coefficients. A processor communicates with the imaging device for receiving the surface temperature. The processor includes computer memory having part characteristics and mathematical equations. The processor uses the measured surface temperature, assumed or measured heat flux or heat transfer coefficients, part characteristics and mathematical equations to determine the flaw characteristics in the part.

16 Claims, 2 Drawing Sheets

U.S. PATENT DOCUMENTS

| | | | |
|---|---|---|---|
| 6,838,670 B2 * | 1/2005 | Lewis et al. | 250/341.6 |
| 7,057,176 B2 * | 6/2006 | Rothenfusser et al. | 250/341.6 |
| 2002/0121602 A1 * | 9/2002 | Thomas et al. | 250/341.6 |
| 2003/0106376 A1 | 6/2003 | Shirzad et al. | |
| 2004/0051035 A1 | 3/2004 | Zombo et al. | |
| 2004/0217289 A1 | 11/2004 | Raulerson et al. | |
| 2004/0245469 A1 | 12/2004 | Favro et al. | |
| 2007/0288177 A1 * | 12/2007 | Rothenfusser et al. | 702/40 |
| 2008/0022775 A1 * | 1/2008 | Sathish et al. | 73/606 |

OTHER PUBLICATIONS

Pye et al., "Heat Emission From Damaged Composite Material and its Use in Non-Destructive Testing", J. Phys. D: Appl. Phys., Issue 5, pp. 927-941, May 14, 1981, Figure 1, pp. 929-940.

European Search Report for EP Application No. 07253415.9, Dec. 19, 2007.

Hamzah et al.: "An Experimental Investigation of Defect Sizing by Transient Thermography", Insight (Non-Destructive Testing and Condition Monitoring), British Institute of Non-Destr. Test., Northampton, GB, vol. 38, No. 3, 1996, pp. 167-170, 173, ISSN:1354-2575.

Rantala et al.: "Amplitude-Modulated Lock-In Vibrothermography for NDE of Polymers and Compsites", Research in Nondestructive Evaluation, Springer Verlag, US, vol. 7, No. 4, 1996, pp. 215-228, ISSN: 0934-9847.

* cited by examiner

INVERSE THERMAL ACOUSTIC IMAGING PART INSPECTION

BACKGROUND OF THE INVENTION

This invention relates to a method and apparatus for inspecting a part to identify, for example, flaws within the part.

Many component parts must be examined to insure that there are no part defects that would compromise their use. This is particularly true in the case of aircraft components such as turbine airfoils. The part must be examined in a non-destructive manner so that the part can still be used after examination. It is difficult to detect some part flaws such as small cracks. Further, any internal part defects may not become evident using traditional non-destructive inspection techniques such as ultrasound, x-ray, fluorescent penetrants or eddy current.

What is needed is a non-destructive inspection method and apparatus that is capable of identifying part flaws such as cracks.

SUMMARY OF THE INVENTION

A method of identifying a flaw in a part is provided that includes vibrating a part to induce heat. The heat originates in any flaws in the part. A thermal image is obtained using, for example, an infrared camera. A mathematical representation, which could be any of a number of analytical modeling methods such as the boundary element method or the finite element method, is used in conjunction with heat transfer equations to identify a source and an intensity of the heat identified with the thermal image. Using the source and intensity of the heat, flaw characteristics for the part can be determined.

The above method is employed using an inspection system that includes a vibration device for vibrating the part. An imaging device, such as an infrared camera, measures the temperature on the surface of the part. A processor communicates with the imaging device for receiving the surface temperature. The processor includes a computer memory having part characteristics and mathematical equations. The processor uses the surface temperature, part and characteristics and mathematical equations to determine the flaw characteristics in the part.

These and other features of the present invention can be best understood from the following specification and drawings, the following of which is a brief description.

DETAILED DESCRIPTION OF THE PREFERRED EMBODIMENT

Figure 1:
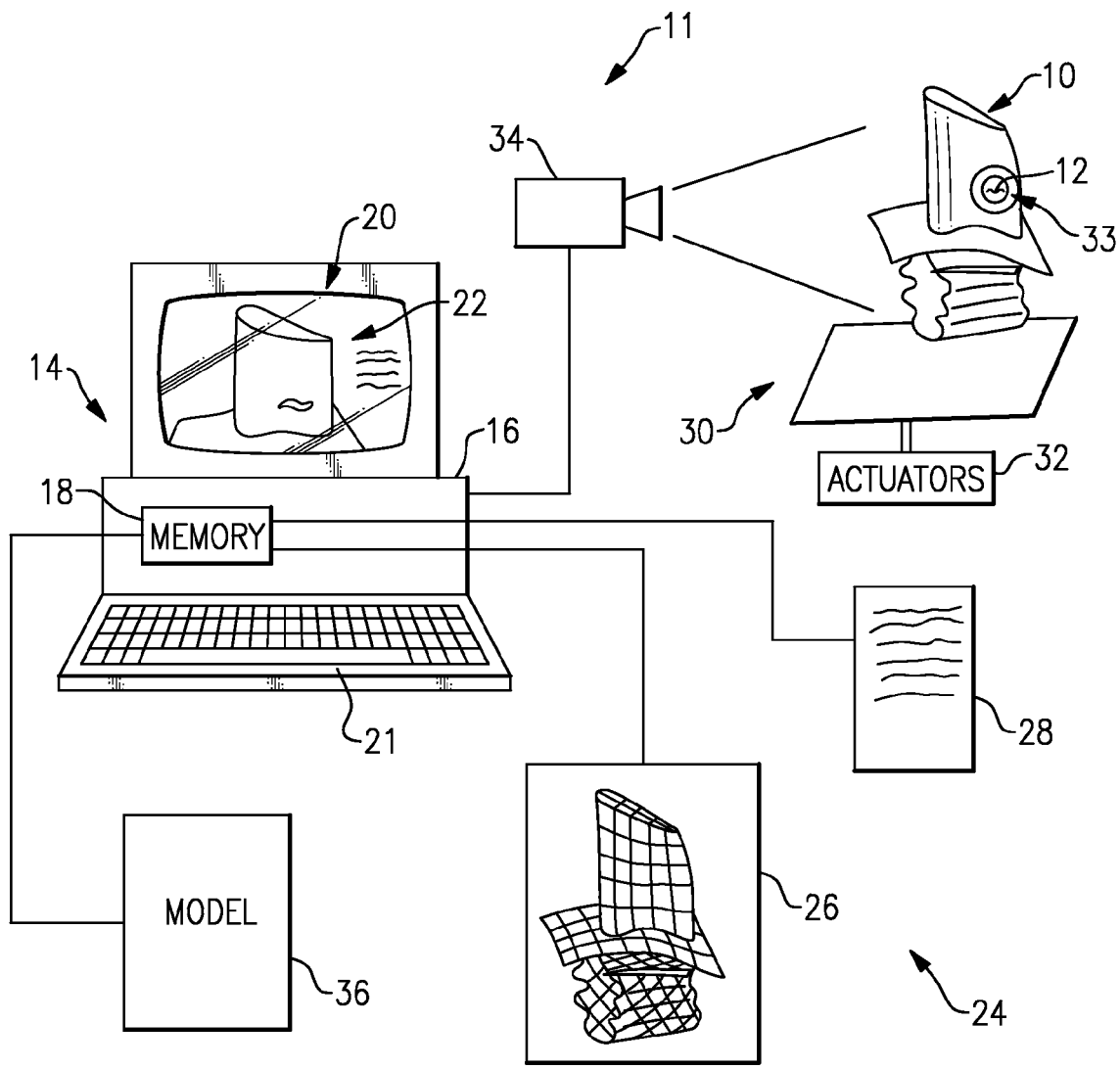
FIG. 1 is a schematic view of an example inspection system used for identifying a flaw in a part.

An inspection system 11 for identifying features within a part 10 such as a flaw is illustrated in FIG. 1. The inspection system 11 can be fully automated. The part 10 having a flaw 12 is mounted on a vibration device 30 that is excited using multiple actuators 32 of different frequency. The vibration device 30 may be a shaker table or ultrasonic devices capable of vibrating the part 10 in a range of, for example, 500 Hz-100 kHz.

Due to the vibration imparted on the part 10 by the vibration device 30, heat is generated at any flaws or cracks within the part 10 due to friction and plastic deformation during each loading cycle. This heating, which is illustrated schematically at 33, results in a temperature rise over the nominal structure temperature of the part 10. The temperature rise caused by a crack is distributed over a range wider than the strained distortion and, hence, can be detected using an infrared camera 34, for example. Images of the exterior of the part 10 are taken by the infrared camera 34. The temperature rise depends upon crack geometry, location, and energy dissipation within the elastic-plastic structure and friction of the flaws banks of the part 10. The energy dissipation or release rate of heat can be parameterized during material modeling, or can be obtained empirically using a known crack geometry. This material information 28 is to be stored in computer memory 18.

A computer 14 is schematically shown in FIG. 1 including a processor 16 and memory 18. The computer 14 includes an output device 20 such as a display. The display 20 can graphically and/or textually illustrate any flaw characteristics 22 identified during the part inspection for subsequent analysis.

In addition to the materials information 28, other part characteristics 24 such as a part model 26 may be provided in the memory 18. The part model 26 can be, for example, boundary element information, which graphically and mathematically represents the structural features of the part 10. The part characteristics 24 can be input into the computer 14 using an input device 21. The memory 18 includes mathematical model 36 that relates the surface temperature information obtained from the infrared camera 34 to one or more flaws within the part 10 using the part characteristics 24.

Figure 2:
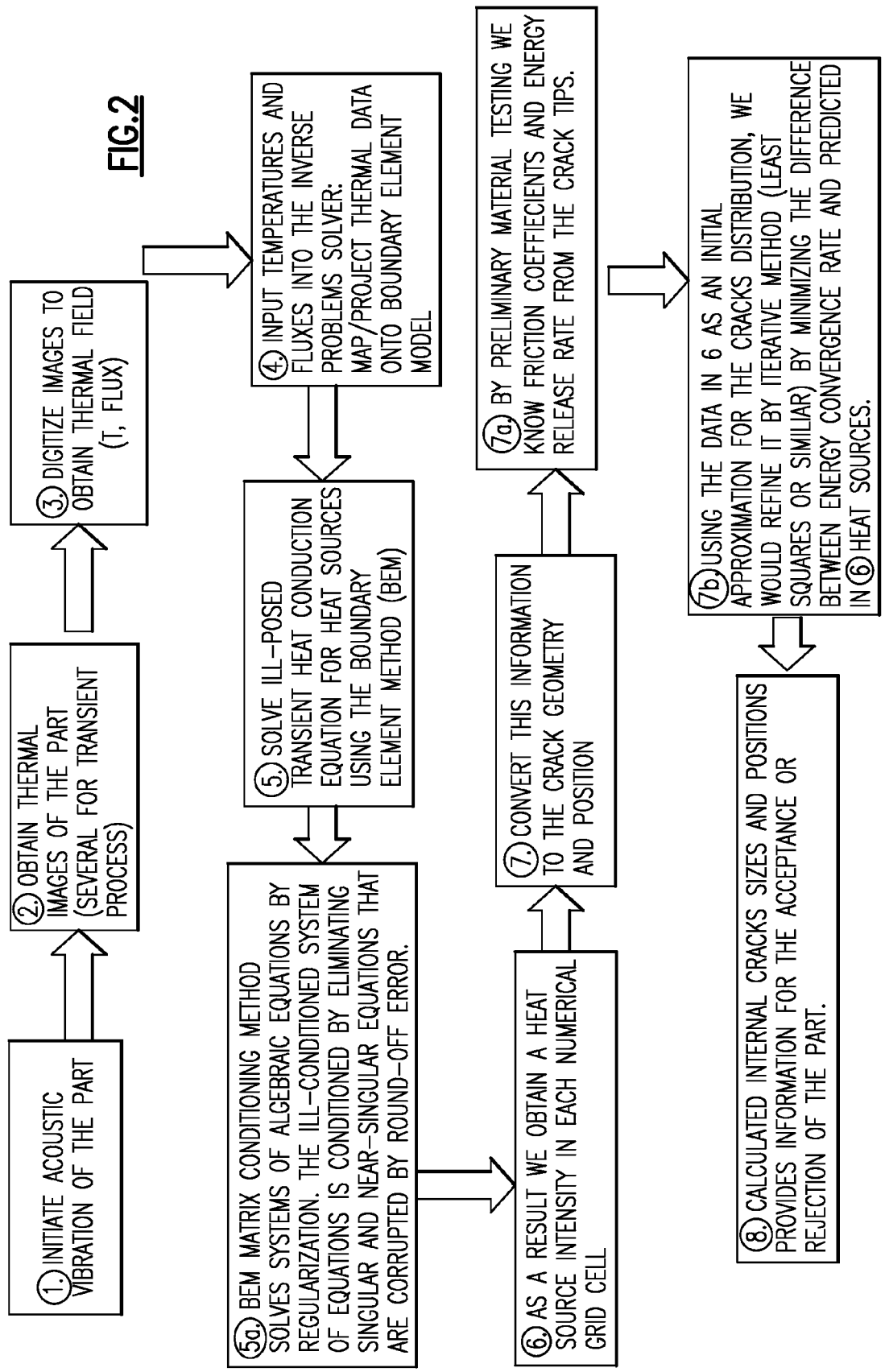
FIG. 2 is a flow chart depicting a method of identifying the flaw in the part.

Referring to FIG. 2, a flow chart illustrating the part inspection procedure is shown. Step 1 includes initiating an acoustic vibration of the part 10 using the vibration device 30. Any surface, sub-surface or buried flaws or cracks will generate heat 33. Step 2 includes obtaining a thermal image of the part 10 using the infrared camera 34. Several images can be taken to capture the transient temperature over the test so it can be compared to the base line temperature of the part 10. The images obtained by the infrared camera 34 are digitized to obtain thermal information such as surface temperature relating to the part 10 in the example illustrated at Step 3. Various sets of digitized thermal images are obtained under different loading conditions such as signal duration, signal parameters and acquisition time, for example.

Step 4 includes using the measured surface temperatures and surface heat fluxes or surface heat transfer coefficients and ambient temperature, either assumed or measured on the surface of the part to inversely solve the transient heat transfer equation to predict unknown heat sources produced by the cracks or flaws. As part of that procedure the thermal information is related to a boundary element model that graphically represents the part 10. Ill-posed transient heat transfer equations of the part 10 are solved for the heat sources in Step 5 using the boundary element method or finite element method, for example. The result of this inverse solution is the prediction of the unknown heat source intensity and locations. A boundary element method matrix conditioning method is used to solve the system of algebraic equations by regularization. The ill-conditioned system of equations is conditioned by eliminating singular and near-singular equations that are corrupted by round-off error, as represented by Step 5A. The heat source intensity is obtained in each numerical grid cell of the boundary element model, as illustrated at Step 6.

Step 7 converts the heat source and intensity information to crack geometry and position information. Step 7A references preliminary material testing and modeling information. The preliminary material information includes known friction coefficients and energy release rates from known crack geometry, which can be gathered empirically and allows an effecting filtering of the initial inverse solution. Step 7B arrives at an initial approximation for the crack distribution. The crack distributions can be refined using an iterative or numerical method such as the method of least squares. The numerical method minimizes the differences between the energy convergence rate and predictions relating to the heat sources. Finally, the internal crack sizes and positions can be calculated. This information is then used to determine whether the part 10 should be accepted or rejected, as indicated at Step 8.

Although an example embodiment of this invention has been disclosed, a worker of ordinary skill in this art would recognize that certain modifications would come within the scope of this invention. For that reason, the following claims should be studied to determine the true scope and content of this invention.

What is claimed is:

1. A method of identifying a flaw in a part comprising the steps of:
    vibrating a part to induce heat at a flaw;
    obtaining a thermal image of the part;
    solving a heat transfer equation based upon a mathematical representation of the part and the thermal image, wherein the heat transfer equation includes a transient inverse heat conduction equation;
    identifying a source and an intensity of the heat corresponding to the flaw;
    determining flaw characteristics from the source and intensity.

2. The method according to claim 1, wherein the thermal image includes surface temperature.

3. The method according to claim 2, wherein the thermal image includes heat flux.

4. The method according to claim 1, wherein the mathematical representation includes a boundary element model, and the thermal image is applied to the boundary element model.

5. The method according to claim 4, wherein the source and intensity of the heat is related to a grid cell from a boundary element model.

6. The method according to claim 1, wherein the heat transfer equation is solved based upon part characteristics including materials information.

7. The method according to claim 6, wherein the materials information includes friction coefficients and energy release rates of the part materials.

8. The method according to claim 1, wherein the transient inverse heat conduction equation is regularized.

9. The method according to claim 1, wherein the flaw characteristics include geometry and position of a crack.

10. The method according to claim 9, wherein a crack distribution is determined using an iterative method.

11. The method according to claim 9, wherein the part is either accepted or rejected based upon the flaw characteristics.

12. An inspection system for a part comprising:
    a vibration device for vibrating the part;
    an imaging device for measuring surface temperature from the part; and
    a processor communicating with the imaging device for receiving the surface temperature, the processor including a memory having part characteristics and mathematical equations, the processor using the surface temperature, part characteristics and mathematical equations to determine flaw characteristics in the part, wherein the mathematical equation includes a transient inverse heat conduction equation.

13. The system according to claim 12, wherein the part characteristics include a boundary element model of the part, friction coefficients of the part and energy release rates of the part.

14. The system according to claim 12, wherein results from the transient inverse heat conduction equation are regularized.

15. The system according to claim 12, wherein the flaw characteristics include crack size and location.

16. The system according to claim 12, wherein the surface temperature is used to determine heat flux, and the part characteristics include heat transfer coefficients.

* * * * *